United States Patent
Okuda et al.

(10) Patent No.: US 6,962,774 B2
(45) Date of Patent: Nov. 8, 2005

(54) METHOD FOR DRY-PRESERVING MULTICELLULAR ORGANISM TISSUE AT ORDINARY TEMPERATURES

(75) Inventors: Takashi Okuda, c/o National Institute of Agrobiological Sciences, 1-2, Ohwashi, Tsukuba-shi, Ibaraki 305-8634 (JP); Masahiko Watanabe, c/o National Institute of Agrobiological Sciences, 1-2, Ohwashi, Tsukuba-shi, Ibaraki 305-8634 (JP); Takahiro Kikawada, c/o National Institute of Agrobiological Sciences, 1-2, Ohwashi, Tsukuba-shi, Ibaraki 305-8634 (JP)

(73) Assignees: National Institute of Agrobiological Sciences, Tsukuba (JP); Takashi Okuda, Tsukuba (JP); Masahiko Watanabe, Tsukuba (JP); Takahiro Kikawada, Tsukuba (JP)

( * ) Notice: Subject to any disclaimer, the term of this patent is extended or adjusted under 35 U.S.C. 154(b) by 0 days.

(21) Appl. No.: 10/659,439

(22) Filed: Sep. 11, 2003

(65) Prior Publication Data

US 2004/0185425 A1 Sep. 23, 2004

(30) Foreign Application Priority Data

Mar. 17, 2003 (JP) .......... 2003-072585

(51) Int. Cl.⁷ .......... A01N 1/02
(52) U.S. Cl. .......... 435/1.1; 435/1.2; 435/1.3; 435/260; 514/568; 514/576

(58) Field of Search .......... 424/410, 403, 424/725; 514/576, 568, 473, 53; 800/288; 530/325; 435/161, 2, 1.3, 260, 1.1, 1.2; 159/48.1

(56) References Cited

PUBLICATIONS

Gordon, S.L. et al. Sep. 2001. Recovery of human mesenchymal stem cells following dehydration and rehydration. (Cryobiology 43(2): 182–187).*

Schwarz, K. Most tolerant of desiccation. in Un. of Florida Book of Insect Records, Chapter 5 © 1994, Gainsville, FL.*

Watanabe, M. et al. 2002. Mechanism allowing an insect to survive complete dehydration and extreme temperatures. (J. Exp. Bio. 205: 2799–2802).*

M. Watanabe, et al., "Mechanism Allowing an Insect to Survive Complete Dehydration and Extreme Temperatures", The Journal of Experimental Biology, vol. 205, No. 18, Sep. 2002, (6 pages including pp. 2799–2802).

* cited by examiner

*Primary Examiner*—Mark Navarro
*Assistant Examiner*—Robert A. Zeman
(74) *Attorney, Agent, or Firm*—Oblon, Spivak, McClelland, Maier & Neustadt, P.C.

(57) ABSTRACT

A tissue of a multicellular organism is gradually dried during cultivation. After the tissue has been completely dehydrated, water is added to the tissue for its recovery. The tissue of the multicellular organism is submerged in an insect body fluid medium treated with heat, and dried for 48 hours or more.

15 Claims, 9 Drawing Sheets

Fig. 1 A small pool dries up in the dry season. *P. vanderplanki* larvae inhabiting in such a pool become completely dried as shown in the pictures, and they are dormant until next rainy season.

Fig. 2

When dried larvae of *P. vanderplanki* are submerged in water, they are recovered within 1 hour and restart their activity.

Fig. 3

- Distilled water
- 2% milk + 1% agar gel

Larvae breeding container (glass bottle with a diameter of 9 cm)

Fig. 4

Imago breeding container

Fig. 5

• Filter paper + 440 µl of distilled water

Drying container (glass petri dish with a diameter of 6 cm)

Time after the start of drying treatment

Variations of trehalose content, while drying, in larvae of *P. vanderplanki* from which the heads and/or thoraxes have been removed

● — Intact larvae (dried)
△ — Decapitated larvae (dried)
○ — Larvae (dried) from which the head and thorax has been removed
□ — Decapitated larvae (non-dried)

Fig. 8

Fluorescence microscopic pictures of fat body dual-stained by CFSE & PI (A-D) and gastrointestinal tract (E-H)
A, E: tissues of living larvae
B, F: tissues of frozen dead larvae
C, G: extirpated tissues that were dried for 2 days
D, H: extirpated tissues that were rapidly dried for half a day
The white line in the picture represents 0.1 mm.

Fig. 9

Upper: Larva of *P. vanderplanki* which was dried after ligation and decapitation
Lower: Larva of *P. vanderplanki* which was recovered when it was submerged in water 7 days later

METHOD FOR DRY-PRESERVING MULTICELLULAR ORGANISM TISSUE AT ORDINARY TEMPERATURES

BACKGROUND OF THE INVENTION

1. Field of the Invention

The present invention relates to a method for dry-preserving a tissue of a multicellular organism at ordinary temperatures.

2. Background Art

The preservation of unicellular organisms can be easily conducted by various methods, but it is common that the preservation of the tissues (organs, meat, fresh vegetables, etc.) of multicellular organisms be conducted under refrigerated or frozen conditions. However, cryopreservation and cryotranport require a huge energy input and refrigerants, which are considered to cause environmental pollution.

Dr. Levine's group at the Center for Molecular Genetics, UCSD School of Medicine, California, USA, introduced and expressed trehalose synthetase derived from $E.$ $coli$ into the muscle fiber cells of humans, resulting in remarkable improvement of the dry resistance of the cells. In other words, after drying the cells for 24 hours, the water content of the cells was measured at almost zero. At that time, the cells were submerged in water. The control cells had all died but 25 to 60% of the cells that expressed trehalose therein indicated life activities (Technical Literature 1).

However, when the drying is conducted for a period exceeding 3 days, the cells exhibited a remarkably low survival rate. This indicates merely that the deactivation of enzyme activity was delayed for a short period by trehalose in dried tissues in a lethal process. When the water content of cells becomes zero, metabolic activities theoretically stop. If the cells have potential recovability at that time, the survival rate should be maintained at a certain level regardless of the time length after drying.

Their results clearly indicate that the accumulation of trehalose is a necessary condition but not a sufficient condition for dry resistance of cells. Their system still has many problems to be solved.

(Technical Literature 1)

Ning Guo et al. (2000) Trehalose expression confers desiccation tolerance on human cells. Nature Biotechnology (18) pp. 168–171

(Technical Literature 2)

Hinton H. E. (1951) A new chironomid from Africa, the larva of which can be dehydrated without injury. Proc. Zool. Soc. Lond. 121, pp. 371–380

(Technical Literature 3)

Denlinger D. L. (1985) Hormonal control of diapause. In Comparative Insect Physiology, Biochemistry and Pharmacology (ed. G. A. Kerkut and L. Gilbert), pp. 354–412. Oxford: Pargamon Press.

SUMMARY OF THE INVENTION

It is an object of the present invention to gradually dry a tissue of a multicellular organism during cultivation, to completely dehydrate the tissue, and then to rehydrate the tissue for recovery.

The present inventors have made intensive efforts to achieve the above object. As a result, they have found conditions for induction of anhydrobiosis, or drying conditions.

Namely, the present invention relates to:

(1) a method for dry-preserving a tissue of a multicellular organism, comprising submerging the tissue of the multicellular organisms in an insect body fluid medium treated with heat, and drying the tissue for 48 hours or more;

(2) a method for dry-preserving a tissue of a multicellular organism, comprising placing a drying container containing a larva of a multicellular organism in a desiccator with a humidity of 5% or less, and evaporating distilled water in the drying container at a rate of 220 to 230 $\mu$l per 24 hours;

(3) the dry-preservation method described in any of (1) or (2) above, wherein the multicellular organism is $Polypedilum$ $vanderplanki;$ and (4) the dry-preservation method described in (3) above, wherein $P.$ $vanderplanki$ is bred at 80% humidity in a 13-hour light/11-hour dark photoperiod.

In the fields of medicine and pharmacology, cultured cells are routinely used for drug experiments or the like. Since long-term preservation technologies are defective, it is necessary to subculture the cells at intervals of several months for the maintenance of the successive generation of cultured cells used therein.

When dry preservation or dry transport of cultured cells is available, the subculturing process of cells can be omitted, thereby allowing great savings of labor costs and utility charges.

Cold preservation or freezing preservation, namely cryopreservation, is the only means for the preservation of tissues and organs (organs and meats). Preservation methods of this type require energy and use environmental pollutants such as chlorofluorocarbon. Further, they have limited preservation periods.

The present inventors have invented a technology which enables the dry preservation of extirpated tissues of multicellular organisms in a recoverable state. The technology requires no energy, is different from the cryopreservation, and enables dry preservation at ordinary temperatures (room temperature). Further, dry preservation in a recoverable state is possible even at high temperatures, such as those in tropical areas. Furthermore, semipermanent preservation is possible.

This technique contributes to technical development for preserving the organs of vertebrate animals. As a result, it is expected that ordinary temperature dry-preservation in the fields of regenerative medicine and food preservation, namely a long-term preservation technique without the need of energy, will be achieved.

The present inventors have repeated the experiments described below and have invented thereby a method comprising extirpating insect tissues, placing these tissues under cultivation, and drying the tissues completely in a recoverable state.

DETAILED DESCRIPTION OF THE INVENTION

EXPERIMENTAL EXAMPLE 1
Selection of Insect Having Strong Resistance to Dryness In considering dry preservation and dry transportation, *Polypedilum vanderplanki*, which inhabits dry regions in Africa and is adapted to an extremely dry environment, was selected.

Figure 1:
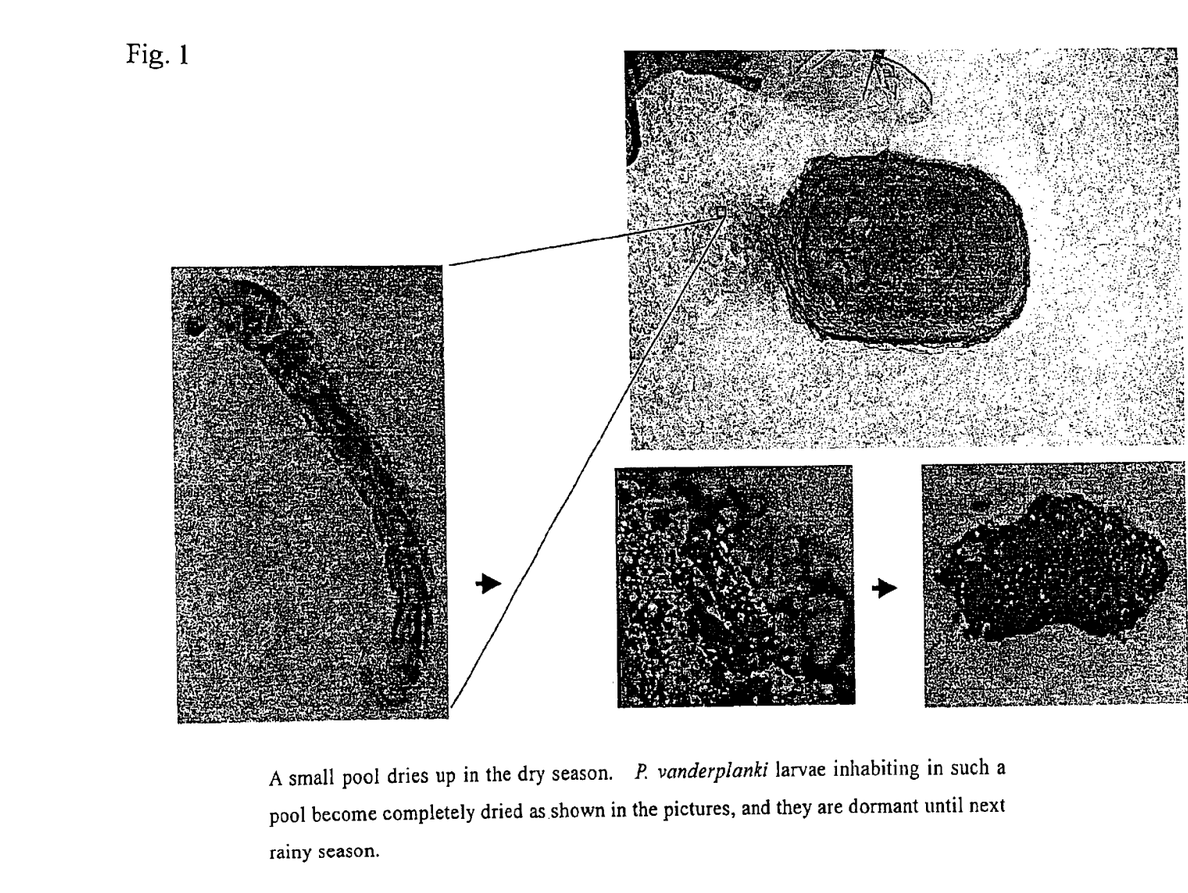
FIG. 1 shows a dormant state of the larvae of $Polypedilum$ $vanderplanki.$
Figure 2:
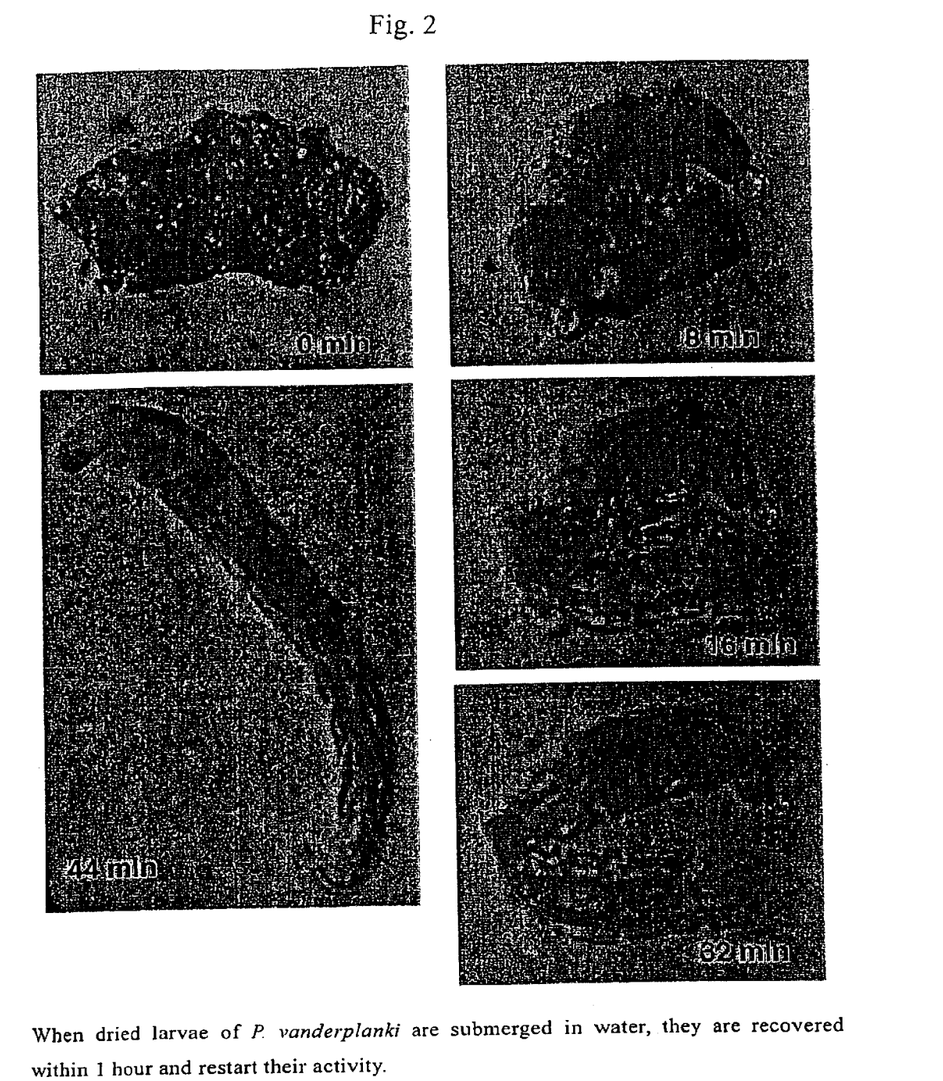
FIG. 2 shows a recovery state of the larvae of $P.$ $vanderplanki.$

Larvae of *P. vanderplanki* live in the water, but their habitat is very unique. They live in small pools left on the craters of rocks. If there is no rain for one week even in a rainy season, such a puddle completely dries up. At that time, the larvae of *P. vanderplanki* become completely dehydrated and wait for the next rain (FIG. 1). After starting water absorption, the dried larvae began their usual aquatic life within 1 hour (FIG. 2). The fact that the present inventors found material having extreme resistance to dryness is one important factor of the present invention.

Hinton, a British scholar, reported about the ability of strong resistance to dryness of *P. vanderplanki* about 50 years ago (Technical literature 2).

However, *P. vanderplanki* is difficult to successively rear indoors, and therefore research on its anhydrobiosis has not been advanced.

The present inventors have established a successive indoor rearing method for *P. vanderplanki* by the following procedure. The breeding is carried out as follows.

Figure 3:
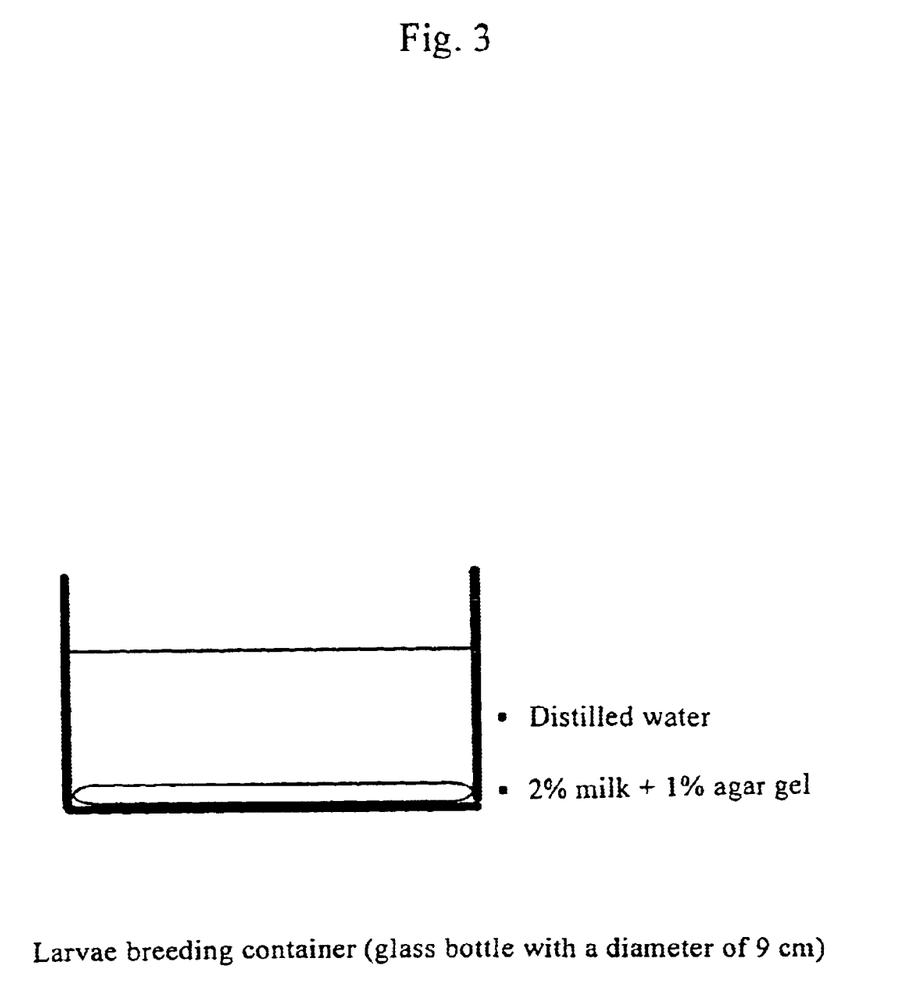
FIG. 3 shows a breeding condition for the larvae.

The larvae were bred, as shown in FIG. 3, under conditions of 80% humidity, a 13-hour light/11-hour dark photoperiod, and with a density of 1 to 2 egg pods per bottle, in a larvae breeding container (a glass bottle with a diameter of 9 cm) containing distilled water, 2% milk, and 1% agar gel. They were aerated continuously.

Figure 4:
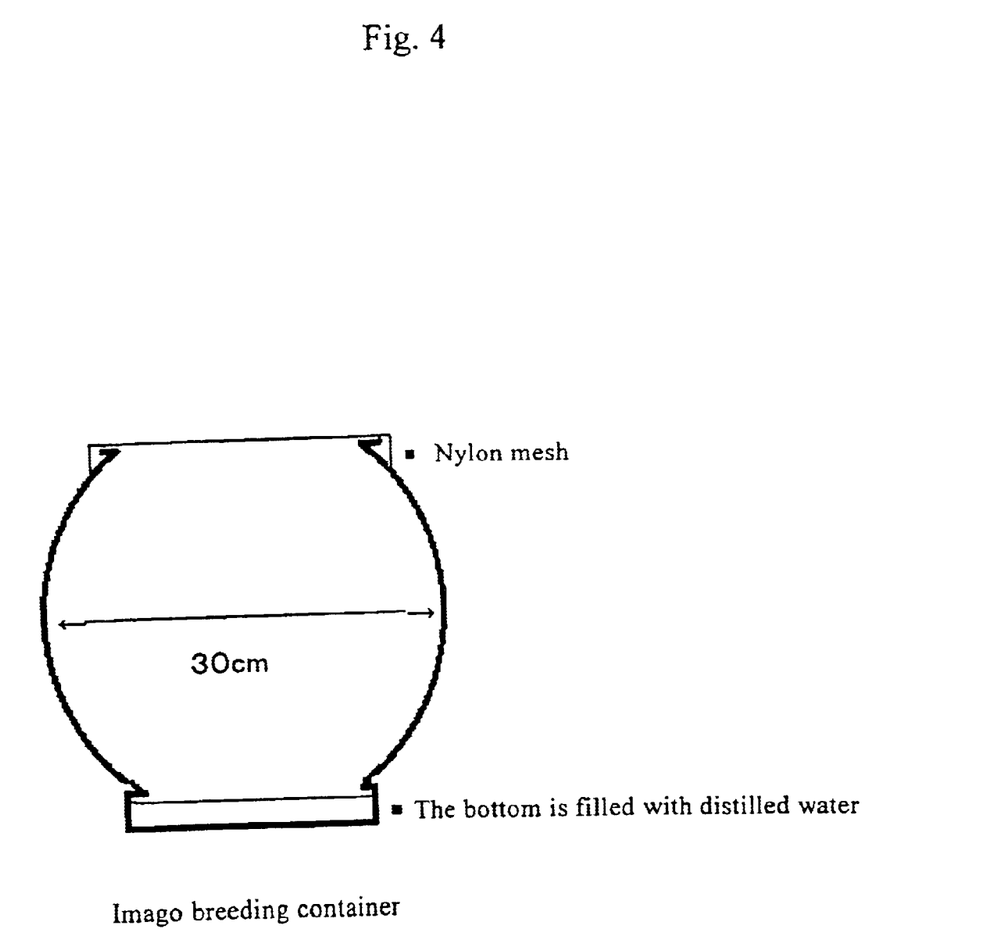
FIG. 4 shows a breeding condition for $P.$ $vanderplanki$ imagoes.

Further, the imagoes were bred, as shown in FIG. 4, under conditions of 80% humidity, a 13-hour light/11-hour dark photoperiod, and with a density of not less than 20 pairs per imago rearing container (40 imagoes in total). Egg pods delivered by them were moved to the larvae breeding container.

EXPERIMENTAL EXAMPLE 2
Conditions for Inducing Anhydrobiosis of Larvae

To determine the conditions for inducting anhydrobiosis of *P. vanderplanki* individuals in the laboratory, the present inventors have conducted the following experiments.

Figure 5:
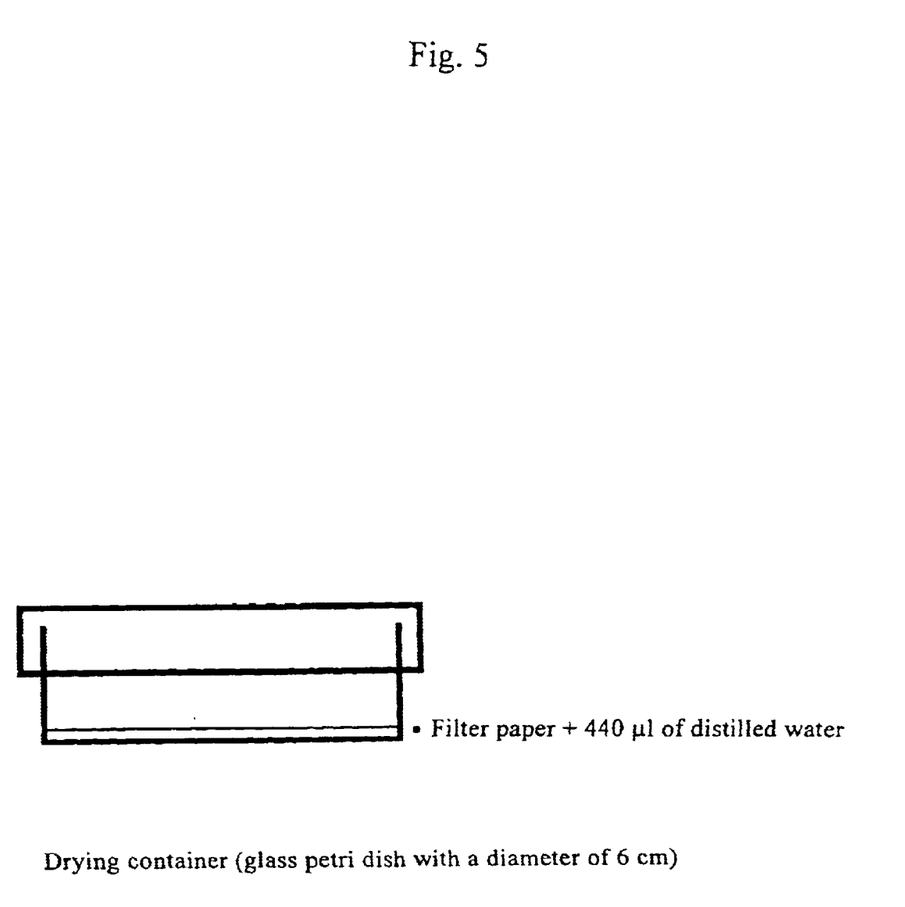
FIG. 5 shows a drying container.

1. 440 $\mu$l of distilled water and a filter paper in a drying container (glass petri dish with a diameter of 6 cm) were arranged as shown in FIG. 5.
2. 10 larvae of *P. vanderplanki* were placed in each drying container.
3. The drying containers were placed in a desiccator at humidity of 5% or less to evaporate the distilled water from the glass petri dish at a rate of about 220 to 230 $\mu$l/day.
4. Consequently, the larvae were completely dehydrated over the course of 2 days while preserving a recoverable state, resulting in anhydrobiosis. Their survival rate was about 80% (FIG. 6).

It should be noted that when larvae were put in 1 ml of distilled water and dried over the course of 24 hours, the dried larvae were not recovered.

Further, the inventors found that a large volume of trehalose was synthesized and accumulated in the process of recoverable anhydrobiosis (equivalent to 20% of dry weight).

Figure 6:
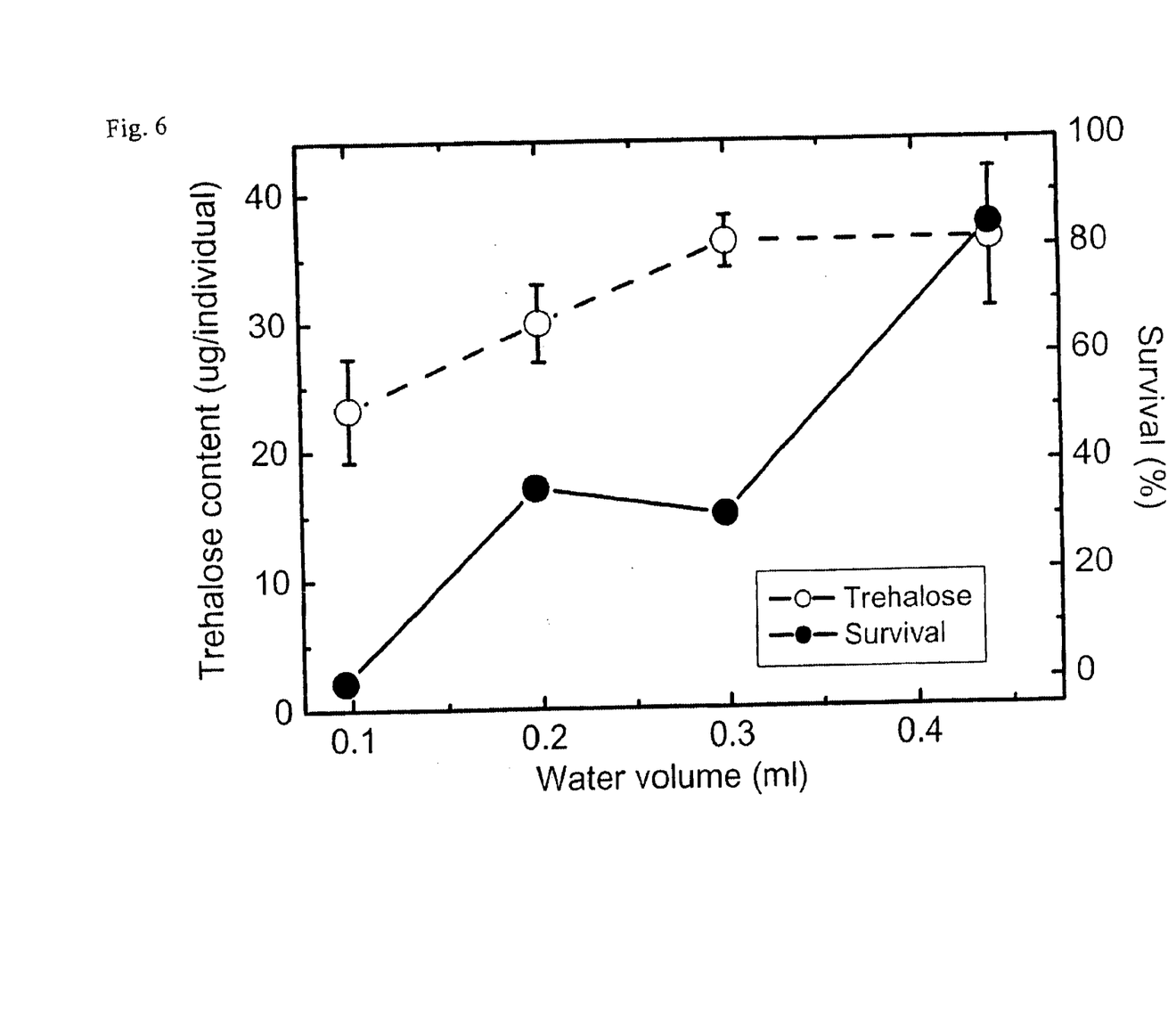
FIG. 6 shows the relationship between water volume, survival rate and trehalose content.

As is clear from FIG. 6, the survival rate became higher and more trehalose was synthesized as the water volume increased. This means that larger water volume lengthens the evaporation period; namely, that the period required for dehydration becomes longer. In this way, sufficient volume of trehalose can be synthesized and accumulated, resulting in a high survival rate.

Figure 7:
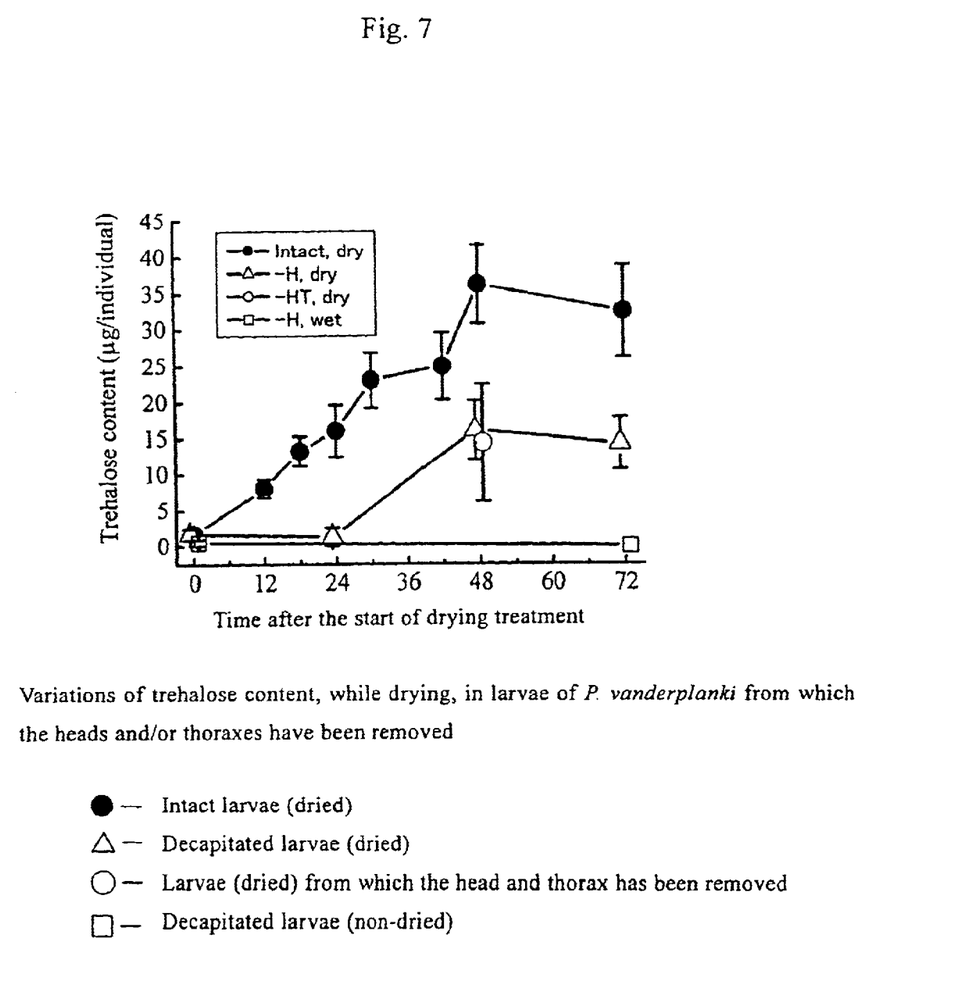
FIG. 7 shows variations of trehalose content while drying larvae of *P. vanderplanki*.

EXPERIMENTAL EXAMPLE 3
Analytical Results of Endocrine Control Mechanism for Trehalose Synthesis Induction (see FIG. 7)

The present inventors have proved that the trehalose synthesis is induced without the mediation of the central nervous system by the following method.

1. Larvae were ligated between the head and thorax with threads and decapitated. These decerebrated larvae could thereafter survive for a few weeks because *P. vanderplanki* is an insect having an open circulatory system.
2. The decerebrated larvae were brought into anhydrobiosis under a rapid drying condition. They were placed in a desiccator for a period of 1 week to 10 days. After it was confirmed that the larvae were completely dried, they were submerged in water (rehydrated). 95% of the decerebrated and dried larvae were recovered.
3. Conventionally, it has been considered that the preparation for the cryptobiosis of insects is advanced through a complex mechanism with the mediation of the central nervous system (Technical literature 3).

However, it has been found in the case of anhydrobiosis of *P. vanderplanki* that the brain is not necessary for the induction of anhydrobiosis. Each tissue therefore responds to dehydration stress, as in the case of plants, and the preparation for anhydrobiosis is self-containedly carried out.

This suggests that extirpated tissues can be dried in a recoverable state.

EXAMPLES

Based on the findings of the above experimental examples, the conditions for drying extirpated tissues (medium composition or dehydration speed, for example) were determined.

Figure 8:
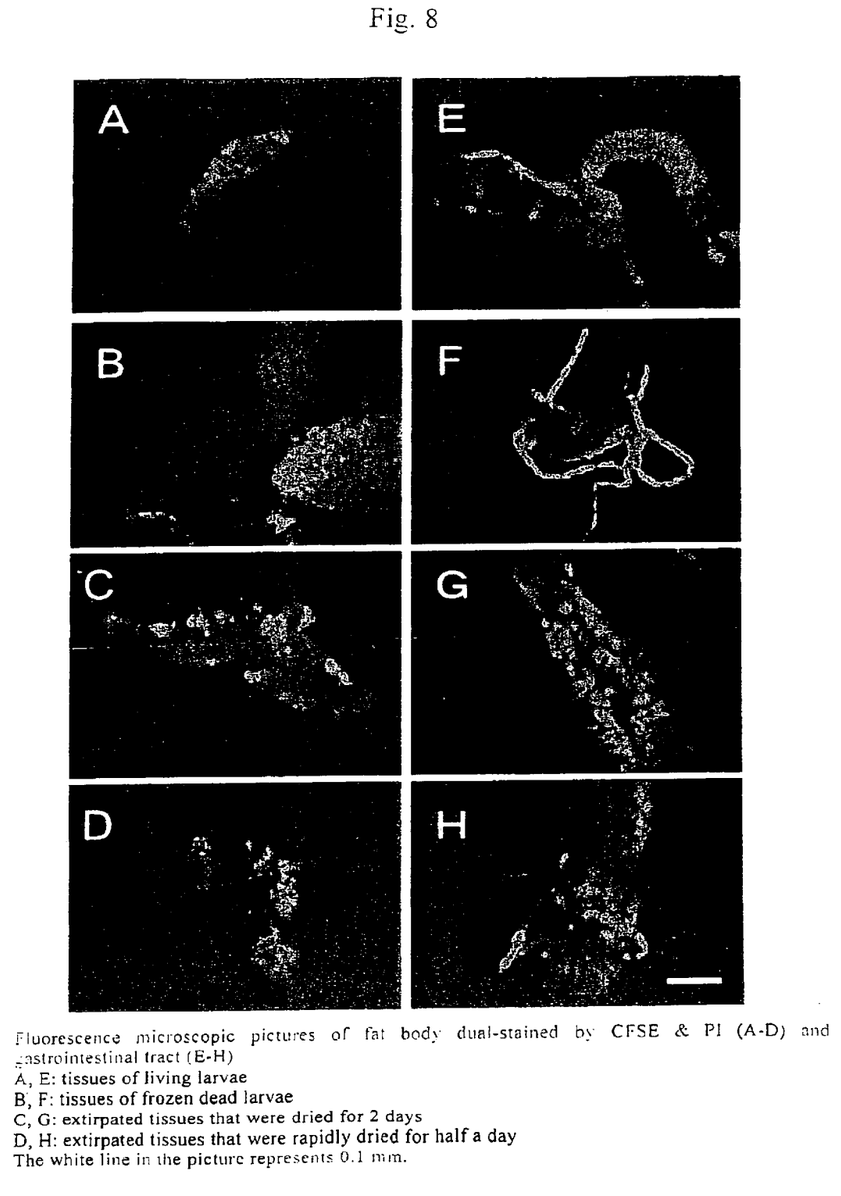
FIG. 8 shows fluorescence microscopic pictures indicating differences in larvae of *Polypedilum vanderplanki* depending on drying conditions.

The present inventors also found that the induction of trehalose synthesis was caused without the mediation of the central nervous system, and thus that it is theoretically possible to dehydrate the extirpated tissues in a recoverable state. Based on the obtained information, the conditions for dehydration of practically extirpated tissues were set. In addition, after these dehydrated tissues were rehydrated, the present inventors established a method of conducting a viability test on these tissues (FIG. 8).

The procedure of a method for dry-preserving tissues of *P. vanderplanki* larvae is as follows.

(a) Final instar larvae were surface-disinfected for 10 seconds with 70% ethanol, and thereafter washed twice with distilled water.

(b) While placing the larvae in the distilled water, the larvae were severed at the abdominal end, and the head, the gastrointestinal tract, the Malpighian tube, and the central nervous system were removed in a mass from the body.

(c) The remaining body parts (mainly fat body and muscle tissue) and the removed gastrointestinal tract were each submerged in 10 µl of heat-treated body fluid medium of an insect (silkworm) dropped on filter paper, and gradually dried over the course of two days.

(d) They were stored in a desiccator for 7 days or 3 months.

(e) 10 µl of PBS was dropped on dried tissues, and they were placed at a humidity of 100% for 1 to 3 hours to determine the viability.

(f) The viability was determined by a dual color fluorescence stain method using carboxyfluorecein diacetate succinimidyl ester (CFSE) and propidium iodide (PI).

Figure 9:
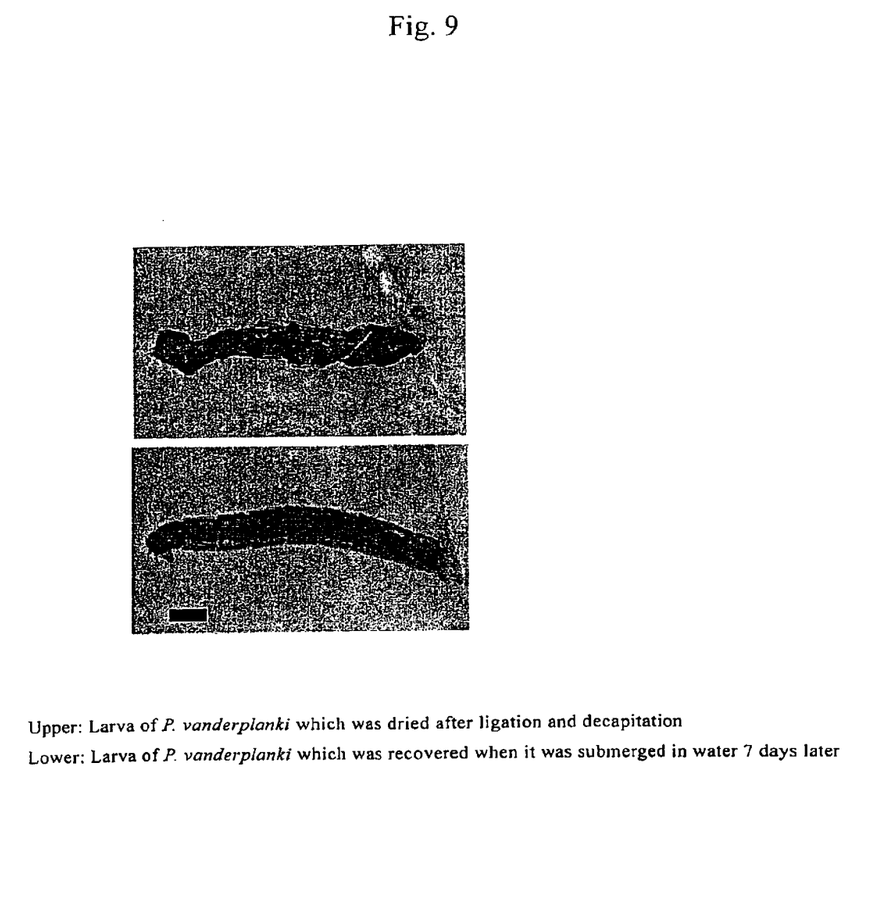
FIG. 9 shows dried and recovered larvae of *P. vanderplanki*.

The extirpated tissues were dried in the medium under the above conditions, and thereafter further placed in the desiccator for a period of 7 days to 3 months. When the dried tissues were then submerged in water, it was confirmed that fat body tissue corresponding to the liver of the vertebrate was recovered (FIG. 9).

With respect to the tissues dry-preserved for 3 months, in other words, regardless of the time length of ordinary temperature dry-preserving, a high survival rate was maintained. This indicates that it is possible to conduct dry-preservation of the extirpated tissues in a recoverable state at ordinary temperatures for a long time by drying the tissues by the use of our method.

Effect of the Invention

According to the present invention, a method for the successive indoor rearing of *P. vanderplanki* has been established. Further, mass reproduction of this insect has become easy due to the determination of induction conditions for anhydrobiosis of *P. vanderplanki* in the laboratory. Therefore, live bait that is dry-preservable for a long period can be supplied to aquarium fish.

Further, the application of this technique can contribute to the development of a preservation technique for organs of vertebrate animals.

Furthermore, the technique is useful as a teaching material for teaching life mechanisms, or physiological mechanisms of dry resistance, heat resistance, cold resistance, and the like.

What is claimed is:

1. A method for dry-preserving tissue of a multicellular organism, comprising:

submerging tissue of the multicellular organism in an insect body fluid medium treated with heat, and drying the tissue for 48 hours or more, wherein said multicellular organism is *Polypedilum vanderplanki* and wherein said tissue is a larval tissue.

2. The dry-preservation method according to claim 1, wherein *Polypedilum vanderplanki* is bred at a humidity of 80% in a 13-hour light/11-hour dark photoperiod.

3. The method of claim 1, comprising dry preserving a larvae.

4. The method of claim 1, comprising dry preserving extirpated tissue.

5. The method of claim 1, further comprising storing in the dry state said tissue after drying.

6. The method of claim 1, further comprising storing said tissue after drying in a desiccator.

7. The method of claim 1, further comprising storing said tissue after drying in the dry state for a period comprising 7 days to 3 months.

8. The method of claim 1, further comprising rehydrating said tissue after drying.

9. The method of claim 1, further comprising rehydrating said tissue after drying and holding said tissue at a humidity of 100% for a period comprising 1 to 3 hours.

10. The method of claim 1, wherein said larval tissue is fat body tissue.

11. The method of claim 1, wherein said larval tissue is muscle tissue.

12. A method for dry-preserving tissue of a multicellular organism, comprising:

placing a drying container containing distilled water and containing a larva or larval tissue of a multicellular organism in a desiccator with a humidity of 5% or less, and evaporating distilled water in the drying container at a rate of 220 to 230 µl per 24 hours, wherein said multicellular organism is *Polypedilum vanderplanki* and wherein said tissue is a larval tissue.

13. The dry-preservation method according to claim 12, wherein *Polypedilum vanderplanki* is bred at a humidity of 80% in a 13-hour light/11-hour dark photoperiod.

14. The method of claim 12, wherein said larval tissue is fat body tissue.

15. The method of claim 12, wherein said larval tissue is muscle tissue.

* * * * *